United States Patent [19]

Ben-Michael

[11] Patent Number: 4,849,342

[45] Date of Patent: Jul. 18, 1989

[54] METHOD FOR CARRYING OUT ENZYME ASSAYS

[75] Inventor: Abraham Ben-Michael, Ramat-Ilan, Israel

[73] Assignee: Savyon Diagnostics Limited, Israel

[21] Appl. No.: 823,367

[22] Filed: Jan. 28, 1986

[30] Foreign Application Priority Data

Jan. 31, 1985 [IL] Israel ................. 74205

[51] Int. Cl.$^4$ .................. G01N 33/535; C12Q 1/26; C12Q 1/28
[52] U.S. Cl. .................. 435/7; 435/25; 435/27; 435/28; 436/826
[58] Field of Search ............ 435/7, 25, 27, 28; 436/826

[56] References Cited

U.S. PATENT DOCUMENTS

| | | | |
|---|---|---|---|
| 3,853,472 | 12/1974 | Rittersdorf | 436/66 |
| 3,986,833 | 10/1976 | Mast | 436/66 |
| 4,071,317 | 1/1978 | Lam | 436/66 |
| 4,071,321 | 1/1978 | Lam | 436/66 |
| 4,148,611 | 4/1979 | Nand | 436/66 |
| 4,278,439 | 7/1981 | White | 435/28 |
| 4,447,542 | 5/1984 | Gantzer | 435/28 |
| 4,615,972 | 10/1986 | Gallacher | 435/7 |
| 4,615,982 | 10/1986 | Lawrence | 436/66 |

FOREIGN PATENT DOCUMENTS

| | | |
|---|---|---|
| 0054358 | 6/1982 | European Pat. Off. . |
| 0103784 | 3/1984 | European Pat. Off. .......... 435/28 |
| 0108526 | 5/1984 | European Pat. Off. . |
| 0116454 | 8/1984 | European Pat. Off. . |
| 0121254 | 10/1984 | European Pat. Off. . |
| 0121317 | 10/1984 | European Pat. Off. . |
| 0123902 | 11/1984 | European Pat. Off. .......... 435/28 |
| 0130520 | 1/1985 | European Pat. Off. .......... 435/28 |
| 0177244 | 4/1986 | European Pat. Off. .......... 435/28 |

OTHER PUBLICATIONS

Inagaki, Chemical Abstracts, 92:2755y (1980).
Sugiura, Chemical Abstracts, 91:86919v (1979).
Thorpe et al., Clin. Chem., 31, 8, 1335–1345 (1985).

*Primary Examiner*—Robert J. Warden
*Assistant Examiner*—Robert Benson
*Attorney, Agent, or Firm*—Lerner, David, Littenberg, Krumholz & Mentlik

[57] ABSTRACT

Peroxidatively active enzyme assays have a variety of clinical and industrial applications. Such assays are based on color development resulting from the addition of the appropriate substrate to the enzyme-containing medium. The stability of the said substrate and the extent of appearance of color are two serious limitations in enzyme assays. A method is disclosed herein for carrying out peroxidatively active enzyme assays when the enzyme is in free solution or in cell-bound form. Stable chemical compositions are also disclosed for use as substrates for carrying out such method.

19 Claims, No Drawings

METHOD FOR CARRYING OUT ENZYME ASSAYS

FIELD OF THE INVENTION

The present invention relates to a method for carrying out enzymes assays and to stable chemical compositions as substrates for carrying out such a method.

BACKGROUND OF THE INVENTION

The above assays exploit the activity of various enzymes toward peroxides, according to the following general reactions:

$$\text{Enzyme} + \text{ROOH} \rightarrow \text{C} + \text{ROH} \quad (I)$$

$$\text{C} + \text{AH}_2 \rightarrow \text{Enzyme} + \text{H}_2\text{O} + \text{A} \quad (II)$$

wherein C represents the enzyme-radical oxygen compound and A is a chromogen material which changes its color due to the loss of the hydrogen atoms.

The enzyme can be any enzyme which is active towards the peroxide, as hereinbefore defined, including but not limited to: peroxidase, catalase and myeloperoxidase. Throughout the following description, peroxidase will be used as the representative enzyme, for the sake of simplicity.

Examples of chromogenic materials are:
chloronaphthol, benzidine, tetramethylbenzidine, 3-amino-9-ethylcarbazole, dichloronaphthol, dibromonaphthol, 3,3',5,5'-tetramethylbenzidine dihydrochloride, 3,3',5,5'-tetramethylbenzidine (dihydrochloride dihydrate), 3-methylbenzothiazole-2,1-hydrazone, parahydroxyphenyl acetic acid, 2,2'-azino-di (3-ethylbenzothiazoline sulfonic acid), 4-aminoantipyrin/-phenol, o-dianizidine, o-toluidine, 5-amino salicylic acid, guaiacol, o-tolidine, pyrogalol.

Examples of commonly employed assays are shortly described hereinafter:

Enzymeimmunoassay (EIA)
In this test, to a medium which is to be checked for the presence of a certain antigen there are added the appropriate insolubilized antibody namely, a peroxidase conjugated antibody. After washing, a substrate containing $H_2O_2$ and a chromogen material is added. In the presence of the tested antigen, the peroxidase conjugated antibody is bound to the antigen. Addition of the substrate causes $H_2O_2$ decomposition by peroxidase with evolution of color.

Immuno-Peroxidase Assay (IPA)
This method employs an antigen, an anti-antigen and a conjugate composed of peroxidase conjugated antibody anti-antibody anti-antigen. The peroxidase is bound and color evolves as above on addition of the substrate.

Peroxidase-anti-peroxidase Method (PAP)
This method commonly employs the reciprocal bonding of the following agents: antigen, anti-antigen (produced in rabbit), goat anti-rabbit IgG and peroxidase-anti-peroxidase (anti-peroxidase produced in rabbit). Binding of peroxidase is again obtained, leading to color development upon addition of the substrate.

In addition to the above assays, there are other extracellular tests which are customarily carried out, e.g., for detecting enzymatic activity in a given medium. In such cases, the substrate is directly added to the enzyme-containing medium and enzyme activity/concentration is obtained from the intensity of the color produced.

The above and similar assays are widely employed today for a variety of clinical tests. The use of these methods, however, is severely hampered by the need to prepare fresh substrate solutions shortly before use, since chromogen materials and peroxides cannot coexist for long periods of time, because of the spontaneous evolution of color which occurs due to the decomposition of the peroxide to give a an oxygen radical, which rapidly occurs under the influence of light, metal ions, impurities etc. A substrate which has spontaneously reacted in such a way cannot be employed to obtain reliable results and has to be replaced.

As it will be apparent to those skilled in the art, it would be highly desirable to be able to obtain a method for carrying out enzyme assays which employs substrates which can be stored prior to use without deteriorating, thereby simplifying and quickening all tests employing them.

In a patent application of the same applicant (namely, U.S. Ser. No. 771,417 filed Aug. 30, 1985), a method and chemical compositions for stabilizing mixtures of chromogen materials and peroxides and stable solutions obtained thereby are described.

SUMMARY OF THE INVENTION

It has been found, and this is an object of the present invention, that it is possible to provide a method for carrying out enzyme assays which employs stable solutions of this kind.

It has also been found, and this is a further object of the invention, that when these solutions are to be used in methods such as that of the present invention i.e. as substrates in biological tests, there are particular composition and conditions requirements, depending on whether they are to be employed in intracellular or extracellular tests.

In particular, it has been found that, when carrying out intracellular assays, the relative the proportions of organic solvent and aqueous solution must lie within a predetermined range, in order to obtain useful staining reactions, and that furthermore that range is different and much more limited, for the range which is desired in performing an intracellular test, as compared to the case with extracellular assays.

The method for carrying out enzyme assays according to the present invention comprises contacting the medium to be tested for enzyme presence with a composition containing:
a. a chromogen compound;
b. a peroxide;
c. a water-miscible organic solvent.
d. an aqueous solvent or a buffer solution; and
e. a compound comprising at least two unsaturations and at least one cyclic moiety selected from among;
a compound of the general formula:

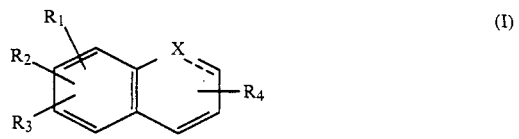

wherein each of $R_1$, $R_2$, $R_3$ and $R_4$ may be independently hydrogen, hydroxy, $CF_3$, halogen, nitro, $SO_2OH$, $NHCH_2CH_2NH_2$ or lower alkyl and X is nitrogen, oxygen, carbon or sulphur;
or a compound of formula

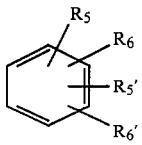

(II)

in which $R_5$, $R_5'$, $R_6$ and $R_6'$ may each be hydrogen, lower alkenyl, —$NH_2$, phenyl optionally substituted, —$NO_2$, halogen, —$OCH_3$, hydroxy, $COOC_6H_5$, COOH, $CH_2COOH$ or $SO_2OH$;

or a compound of formula

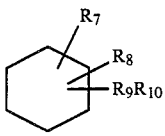

(III)

in which $R_7$ and $R_8$ may each be hydroxy or lower alkenyl, $R_9$ is alkenyl and $R_{10}$ is an azulene group optionally substituted by one or more straight or branched alkyl group of $C_1$–$C_{10}$;

or a compound of formula

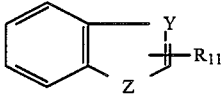

(IV)

wherein Y and Z may each be oxygen, nitrogen or sulfur and $R_{11}$ is hydrogen or hydroxyphenyl;

or a compound of formula

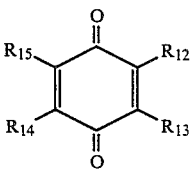

(V)

wherein each of $R_{12}$, $R_{13}$, $R_{14}$ and $R_{15}$ may independently be hydrogen, hydroxy or lower alkyl;

or a salt of one of compounds (I), (II), (III), (IV) or (V); and checking whether color is evolved.

The water-miscible organic solvent preferably has a gas-phase dipole moment equal to or greater than 1.60 D.

According to a preferred embodiment of the invention, the enzyme is selected from among; peroxidase, catalase and myeloperoxidase.

The method according to the invention can be usefully employed in intracellular assays, e.g., when the assay is IPA or PAP. According to a preferred embodiment of the invention, the method is further usefully employed when the assay to be carried out is an extracellular enzymatic activity test, e.g., EIA. According to a preferred embodiment of the invention, when the assay is an intracellular assay the ratio between the organic solvent and the aqueous solution is between 45:55 and 25:75, preferably about 35:65, volume percent.

According to still another preferred embodiment of the invention, when the assay is an extracellular assay the ratio between the organic solvent and the aqueous solution is between 80:20 and 20:80, volume percent. It has been found that in both intracellular and extracellular assays dimethylsulfoxide is particularly convenient as the organic solvent.

The chemical composition for carrying out the method according to the invention is characterized in that it contains:

a. a chromogen compound;
b. a peroxide;
c. a water-miscible organic solvent.
d. an aqueous solvent or a buffer solution; and
e. a compound of the general formula (I), (II), (III), (IV) or (V), as defined above, or a salt of these compounds.

This composition may further contain in the aqueous solution 0 to 5000 ppm of chelating agents. The chelating agents are preferably selected from pyrophosphate, acetanilide, citrate or 8-hydroxyquinoline, either alone or in admixture of two or more of such chelating agents.

According to a preferred embodiment of the invention the said compositions contain:

0 to 200 ppm pyrophosphate
0 to 200 ppm acetanilide
0 to 1000 ppm citrate
0 to 2000 ppm 8-hydroxyquinoline or a hemi-sulfate salt thereof.

The water-miscible organic solvent preferably has a dipole moment equal to or greater than 1.60 D;

The organic solvent is preferably selected from methanol, ethanol, dioxane, dimethylsulfoxide, sulfolane, dimethylsulfone, hexamethylphosphoric triamide or dimethylformamide.

The compound of formula (I) is preferably selected from among 8-hydroxyquinoline, 4-chloro-7-(trifluoromethyl) quinoline, 5-chloro-7-iodo-8-hydroxyquinoline, 5-chloro-8-hydroxyquinoline or a copper or hemi-sulphate salt of 8-hydroxyquinoline.

The compound of formula (II) is preferably 4-anilino sulfonic acid and the compound of formula (III) is preferably Colecalciferol.

The buffer is preferably selected from among: phosphate buffer (PB), Tris buffer (hydroxymethylaminomethane), borate buffer and glycine buffer.

The chromogen material is preferably selected from the group comprising:

chloronaphthol, benzidine, tetramethylbenzidine, 3-amino-9-ethylcarbazole, dichloronaphthol, dibromonaphthol, 3,3',5,5'-tetramethylbenzidine dihydrochloride, 3,3',5,5'-tetramethylbenzidine (dihydrochloride dihydrate) 3-methylbenzothiazole-2,1-hydrazone, parahydroxyphenyl acetic acid, 2,2'-azino-di(3-ethylbenzothiazoline sulfonic acid),4-aminoantipyrin/-phenol, o-dianizidine, o-toluidine, 5-amino salicilic acid, guaiacol, o-tolidine, pyrogalol.

According to a preferred embodiment of the invention, the ratio between the organic solvent and the aqueous solution is between 45:55 and 25:75, volume percent, preferably about 35:65, volume percent.

According to another preferred embodiment of the invention, the ratio between the organic solvent and the aqueous solution is between 80:20 and 20:80, volume percent.

The pH of the said compositions should be between 7 and 8, preferably about 7.6.

All the aforesaid and other characteristics and advantages of the invention will be better understood from the following illustrative and non limitative examples.

EXAMPLES 1–15

The following examples are illustrative of the intracellular/extracellular action of the compositions of the invention.

Several compositions were prepared using Dimethylsulfoxide (DMSO) as the organic solvent and a tris buffer, and varying their volumetric ratio. All compositions contained the following materials: 100 mg 8-hydroxyquinoline-hemi-sulphate salt, 500 mg 4-chloro-1-naphthol, distilled water, 80 mg acetanilide, 80 mg pyrophosphate and 800 mg citrate. The total volume of water and DMSO was 1 liter.

The resulting compositions were top-desk stored for one month and used to carry out comparison tests for presence of peroxidase both in cellular-bound form and in free solution (horseradish). the results of these tests, in terms of relative staining, are detailed in Table 1.

TABLE 1

| Run No. | DMSO vol % | bound | free |
| --- | --- | --- | --- |
| 1 | 10 | faint | faint |
| 2 | 20 | faint | fair |
| 3 | 25 | fair | strong |
| 4 | 30 | strong | strong |
| 5 | 35 | strong | strong |
| 6 | 40 | strong | strong |
| 7 | 45 | fair | strong |
| 8 | 50 | faint | strong |
| 9 | 55 | — | strong |
| 10 | 60 | — | strong |
| 11 | 65 | — | strong |
| 12 | 70 | — | strong |
| 13 | 75 | — | fair |
| 14 | 80 | — | fair |
| 15 | 85 | — | faint |

EXAMPLE 16

An EIA test was carried out for the determination of human chorionic gonadotropin, employing 4-aminoantipyrin/phenol as the chromogen, and employing a composition similar to that of the preceding examples, with a DMSO content of 35%.

Upon application of the substrate, a pink color developed. The bound peroxidase content was estimated by spectrophotometry at 510 nm.

EXAMPLE 17

The test of Example 16 was repeated using o-dianizidine as the chromogen but with a DMSO content of 30%. Colour evolved and was read at 400 nm.

EXAMPLE 18

The test of Example 16 was repeated using 5-aminosalycilic acid as the chromogen. Concentration was estimated by reading the absorbance at 540 nm.

EXAMPLE 19

An IPA test was carried out for the determination of Chlamydia Trachomatis, in a composition similar to that of Examples 1–15, with an DMF content of 35%. the chromogen employed was 4-chloro-1-naphthol. Upon addition of the substrate, an insoluble ultramarine colored complex was obtained.

EXAMPLE 20

A PAP test was carried out with a DMSO content of 25%, employing 4-chloro-1-naphthol as a chromogen for the determination of Epstein Bar. Upon addition of the substrate, an insoluble complex of ultramarine color was obtained.

EXAMPLES 21–23

A solution was tested for estimating the contents of peroxidase produced from horseradish. Three different tests were carried out employing ethanol as the solvent with a 65% contents relative to the buffer, using 4-chloro-1-naphthol, o-dianizidine and guaiacol as the three different chromogens. All three tests gave comparable results.

COMPARATIVE TESTING

All of the above examples were carried out both with freshly prepared and with weeks-old substrates which were desk-stored. No detectable difference was found between the results obtained with freshly prepared compositions and with compositions prepared several weeks before.

What we claim is:

1. A method for carrying out assays for peroxidase, catalase, and myeloperoxidase in which a chromogen compound changes its color when reacted with a peroxide in the presence of a peroxidatively active enzyme selected from the group consisting of peroxidase, catalase, and myeloperoxidase, said reaction between said chromogen compound and said peroxide being catalyzed by said enzyme, comprising contacting a sample to be tested for enzyme presence with a liquid solution composition consisting essentially of:
   a. a chromogen compound;
   b. a peroxide;
   c. a water-miscible organic solvent;
   d. water or a buffer solution; and
   e. a compound soluble in said organic solvent of the general formula

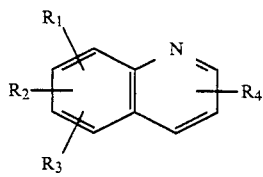

wherein each of $R_1$, $R_2$, $R_3$ and $R_4$ is independently selected from the group consisting of hydrogen, hydroxy, $CF_3$, halogen, nitro, $SO_2OH$, $NHCH_2CH_2NH_2$ and lower alkyl, or with a salt of the above formula and relating the degree of color change to the amount of said enzyme in said sample, wherein the ratio between said organic solvent and said water solution is between about 45:55 and about 25:75, volume percent, respectively, when said assay is an intra-cellular assay, and wherein the ratio between said organic solvent and said water solution is between about 80:20 and about 20:80, volume percent, respectively, when said assay is an extra-cellular assay.

2. A method according to claim 1 wherein said water-miscible organic solvent has a gas-phase dipole moment equal to or greater than 1.60 D.

3. A method according to claim 1 wherein said assay is an intracellular assay.

4. A method according to claim 1, wherein the ratio between said organic solvent and said aqueous solvent medium is about 35:65 volume percent.

5. A method according to claim 1 wherein said organic solvent is dimethylsulfoxide.

6. A method according to claim 1, including adding to said water or buffer solution up to 5000 ppm of one or more chelating agents selected from the group consisting of sodium pyrophosphate, acetanilide, sodium citrate, 8-hydroxyquinoline and the hemisulfate salts thereof.

7. A method according to claim 6 comprising adding to said water or buffer solution chelating agents comprising up to 200 ppm sodium pyrophosphate, up to 200 ppm acetanilide, up to 1000 ppm sodium citrate, and up to 2000 ppm 8-hydroxyquinoline or a hemi-sulfate salt thereof.

8. A method according to claim 1, wherein $R_4$ comprises hydrogen.

9. The method of claim 8 wherein $R_1$, $R_2$ and $R_3$ are selected from the group consisting of hydrogen, hydroxy, $CF_3$, and halogen.

10. A method according to claim 1 or 3 wherein said organic solvent is selected from the group consisting of methanol, ethanol, dioxane, dimethylsulfoxide, sulfolane, dimethylsulfone, hexamethylphosphoric triamide and dimethylformamide.

11. A method according to claim 1 or 3 wherein said compound of formula (I) is selected from the group consisting of 8-hydroxyquinoline, 4-chloro-7-(trifluoromethyl) quinoline, 5-chloro-7-iodo-8-hydroxyquinoline, 5-chloro-8-hydroxyquinoline and the hemisulphate salts of 8-hydroxyquinoline.

12. A method according to claim 1 or 3 wherein said buffer is selected from the group consisting of phosphate buffer (PB), Tris buffer, borate buffer and glycine buffer.

13. A method according to claim 1 or 3, wherein said chromogen material is selected from the group consisting of 4-chloro-1-naphthol, 3,3′,5,5′-tetramethylbenzidine, 3-amino-9-ethylcarbazole, 3,3′,5,5′-tetramethylbenzidine dihydrochloride, 3,3′,5,5′-tetramethylbenzidine(dihydrochloride dihydrate), 3-methylbenzothiazole-2,1-hydrazone, parahydroxyphenyl acetic acid, 2,2′-azino-di-(3-ethylbenzothiazoline sulfonic acid), mixtures of 4-aminoantipyrine and phenol, 0-dianizidine, o-toluidine, 5-amino salycilic acid, quaiacol, o-tolidine and pyrogalol.

14. In the enzyme immunoassay in which a chromogen compound changes its color when reacted with a peroxide in the present of a peroxidatively active conjugated enzyme selected from the group consisting of peroxidase, catalase and myeloperoxidase, said enzyme being chemically conjugated to an antibody or an antigen, said reaction between said chromogen compound and said peroxide being catalyzed by said conjugated enzyme, the improvement comprising contacting a sample to be tested for conjugated enzyme presence with a liquid solution composition consisting essentially of:
a. said chromogen compound;
b. a peroxide;
c. a water-miscible organic solvent;
d. water or a buffer solution;
e. a compound soluble in said organic solvent of the general formula

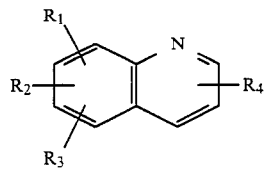

wherein each of $R_1$, $R_2$, $R_3$ and $R_4$ is independenttly selected from the group consisting of hydrogen, hydroxy, $CF_3$, halogen, nitro, $SO_2OH$, $NHCH_2CH_2NH_2$ lower alkyl, or with a salt of the compound of the above formula and relating the degree of color change to the amount of said enzyme conjugated to said antibody or said antigen in said sample, wherein the ratio between said organic solvent and said water solution is between about 45:55 and about 25:75, volume percent, respectively, when said assay is an intra-cellular assay, and wherein the ratio between said organic solvent and said water solution is between about 80:20 and about 20:80, volume percent, respectively, when said assay is an extra-cellular assay.

15. In the enzyme immunoassay of claim 14 improvement wherein $R_4$ comprises hydrogen.

16. In the enzyme immunoassay of claim 15 improvement wherein $R_1$, $R_2$ and $R_3$ are selected from the group consisting of hydrogen, hydroxy, $CF_3$ and halogen.

17. In the peroxidase-anti-peroxidase method of carrying out assays in which a chromogen compound changes its color when reacted with a peroxide in the presence of a peroxidatively active bound enzyme comprising peroxidase bound to an anti-peroxidase antibody, reaction between said chromogen compound and said peroxide being catalyzed by said bound enzyme, the improvement comprising contacting a sample to be tested for bound enzyme presence with a liquid solution composition consisting essentially of:
a. said chromogen compound;
b. a peroxide;
c. a water-miscible organic solvent;
d. water or a buffer solution;
e. a compound soluble in said organic solvent of the general formula

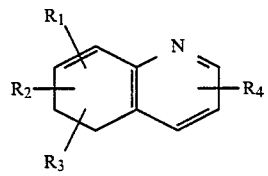

wherein each of $R_1$, $R_2$, $R_3$ and $R_4$ is independently selected from the group consisting of hydrogen, hydroxy, $CF_3$, halogen, nitro, $SO_2OH$, $NHCH_2CH_2NH_2$ and lower alkyl, or with a salt of the compound of the above formula and relating the degree of color change to the amount of said enzyme bound to said anti-peroxidase antibody in said sample, wherein the ratio between said organic solvent and said water solution is between about 45:55 and about 25:75, volume percent, respectively, when said assay is an intra-cellular assay, and wherein the ratio between said organic solvent and said water solution is between about 80:20 and about 20:80, volume percent, respectively, when said assay is an extra-cellular assay.

18. In the peroxidase-anti-peroxidase method of claim 17 the improvement wherein $R_4$ comprises hydrogen.

19. In the peroxidase-anti-peroxidase method of claim 18 the improvement wherein $R_1$, $R_2$ and $R_3$ are selected from the group consisting of hydrogen, hydroxy $CF_3$ and halogen.

* * * * *